United States Patent [19]

Kawamata et al.

[11] Patent Number: 4,459,234

[45] Date of Patent: Jul. 10, 1984

[54] PROCESS FOR PRODUCING ANTHRAQUINONE

[75] Inventors: Motoo Kawamata; Shiro Fujikake, both of Yokohama, Japan

[73] Assignee: Mitsui Toatsu Chemicals, Inc., Tokyo, Japan

[21] Appl. No.: 154,929

[22] Filed: May 30, 1980

[51] Int. Cl.$^3$ .............................................. C07C 49/68
[52] U.S. Cl. .................................................. 260/369
[58] Field of Search ................ 260/369; 252/461, 436, 252/440

[56] References Cited

U.S. PATENT DOCUMENTS

| | | | |
|---|---|---|---|
| 3,173,913 | 3/1965 | Stelt | 260/369 |
| 3,507,813 | 4/1970 | Harvey | 252/461 |
| 3,658,893 | 4/1972 | Sturm et al. | 260/369 |
| 3,699,134 | 10/1972 | Armbrust et al. | 260/369 |
| 4,036,783 | 7/1977 | Blechschmitt et al. | 252/461 |
| 4,036,860 | 7/1977 | Engelbach et al. | 260/369 |

FOREIGN PATENT DOCUMENTS

| | | |
|---|---|---|
| 49-30350 | 3/1974 | Japan . |
| 49-10749 | 9/1974 | Japan . |
| 49-95952 | 9/1974 | Japan . |

*Primary Examiner*—Paul F. Shaver
*Attorney, Agent, or Firm*—Fisher, Christen & Sabol

[57] ABSTRACT

A novel process for producing anthraquinone in good yields is provided which comprises reacting phthalic anhydride with benzene in a single step in the vapor phase in the presence of a catalyst comprising titanium oxide and/or tin oxide.

13 Claims, No Drawings

PROCESS FOR PRODUCING ANTHRAQUINONE

This invention relates to a process for producing anthraquinone from phthalic anhydride and benzene using a novel catalyst.

Commercial production of anthraquinone has previously relied mainly on the oxidation of anthracene. This method, however, is not entirely satisfactory because the supply of the starting anthracene is not stable. Another known method for producing anthraquinone comprises reacting phthalic anhydride and benzene using aluminum chloride and sulfuric acid as catalysts. This method is not economically advantageous since it comprises two steps and a large quantity of aluminum chloride is consumed.

As an improvement of the aforesaid method, Japanese Laid-Open Patent Publication No. 30350/74 discloses a method which comprises reacting phthalic anhydride and benzene in the vapor phase using a catalyst comprising a crystalline aluminosilicate. This method is neither feasible for practical application because the activity of the catalyst is not sufficient, and even when the mole ratio of benzene to phthalic anhydride is adjusted to as high as 46, the conversion of phthalic anhydride into anthraquinone is as low as about 15%.

It is an object of this invention to provide a process for producing anthraquinone in a single step from phthalic anhydride and benzene.

In accordance with this invention, this object is achieved by a novel process for producing anthraquinone in a single step which comprises reacting phthalic anhydride with benzene in the vapor phase in the presence of a catalyst comprising titanium oxide and/or tin oxide.

The process of this invention brings about the following commercial advantages over a conventional method for producing anthraquinone from phthalic anhydride and benzene in the presence of aluminum chloride.

(1) The catalyst (titanium oxide and/or tin oxide) is stable unlike aluminum chloride, and a sufficient effect can be obtained by using it in a catalytic amount.

(2) Anthraquinone can be produced in the vapor phase in a single step.

(3) The yield of anthraquinone is very high.

The catalyst used in this invention comprises titanium oxide or tin oxide or both. Titanium hydroxide, titanium chloride, titanium oxide, titanyl sulfate, titanic acid, etc. can be used as sources of titanium for catalyst preparation, and tin oxide, tin chloride, tin sulfate, tin hydroxide, meta-stannic acid, etc. can be used as sources of tin. Methods for producing known metallic oxide catalysts can be applied to the production of the catalyst used in this invention, and methods of precipitation, gellation or impregnation, for example, are suitable. The catalyst prepared by such methods is generally dried at a temperature of less than about 150° C., then calcined at a temperature of about 300° C. to about 700° C., and molded by various methods such as tableting or pulverization and screening. The final catalyst obtained can be used in the process of this invention. Or it is possible to support a titanium compound and/or a tin compound in paste form on a suitable carrier such as alumina, silica, carborundum or steatite and calcining the supported product to a final catalyst for use in this invention. Alternatively, a solution of a titanium compound and/or a tin compound is impregnated in a porous carrier and a precipitate is formed by a suitable method such as pH adjustment, followed by drying and calcination to form a final catalyst which can be used in this invention.

The catalyst used in the process of this invention comprises titanium oxide and/or tin oxide. The activity of the catalyst may be increased by including a small amount of another ingredient such as molybdenum oxide, tungsten oxide, vanadium oxide, iron oxide, chromium oxide, manganese oxide, etc. If desired, an alkali metal oxide or an alkaline-earth metal oxide may be added to enhance the moldability and stability of the catalyst. Inclusion of a sulfuric acid radical in the catalyst of this invention leads to the increase of the activity of the catalyst and the durability of its activity. The amount of the sulfuric acid radical included is preferably 0.1 to 50 moles per 100 moles of tin oxide titanium oxide and/or tin oxide.

Good results of reaction can be obtained in the process of this invention if the starting phthalic anhydride and benzene are pure. Since, however, crude benzene containing various aromatic hydrocarbons attributed to the process of benzene production and crude phthalic anhydride containing aliphatic and aromatic carboxylic acids or other by-products attributed to the process of phthalic anhydride production do not substantially effect the reaction adversely, the starting materials containing considerable amounts of the aforesaid impurities may be used in the reaction in accordance with this invention. The mole ratio of phthalic anhydride to benzene may be 1:1, but generally, benzene is desirably used in excess. For practical purposes, the suitable mole ratio of phthalic anhydride to benzene is from 1:3 to 1:30.

The temperature at which the reaction in accordance with this invention is carried out is generally in the range of 300° to 600° C., preferably 350° to 550° C. Temperatures exceeding the upper limit are undesirable because the selectivity for anthraquinone formation decreases, and the proportion of side-reactions such as decarboxylation of phthalic anhydride increases. Temperatures below the lower limit of the specified range are neither desirable since a sufficient rate of reaction cannot be obtained, and the proportion of reaction intermediates increases. The optimal reaction temperature is correlated with the rate of feeding the materials with respect to the amount of the catalyst used (for example, gas space velocity GHSV). Usually, space velocities (SV) of 500 to 10000 $hr^{-1}$ are used. It is necessary, however, to maintain good results of the reaction by adjusting the reaction temperature at a higher point when the SV is higher and to a lower point when SV is lower.

The reaction in accordance with this invention can be performed either at atmospheric pressure or at elevated pressures. Sometimes, it may be carried out at lower pressures than atmospheric pressure. Generally, the reaction is carried out in a fixed bed, but a fluidized bed or a moving bed can also be used. In feeding the reaction materials, an inert gas such as nitrogen or carbon dioxide gas may be used as a diluent. Carbon dioxide gas is an especially favorable diluent because it can inhibit decarboxylation of phthalic anhydride and increase the conversion of phthalic anhydride into anthraquinone.

The reaction product obtained by the method described hereinabove is then purified by various known methods such as distillation, crystallization, sublimation or adsorption for separation of by-products. Thus, anthraquinone of high purity can be obtained.

The following Examples illustrate the present invention specifically. In these examples, all percentages are by weight.

EXAMPLE 1

Refined meta-titanic acid ($TiO_2$ content 83.5%) obtained by sufficiently washing meta-titanic acid (a product of Fuji Titanium Co., Ltd.) with water and then drying it at 130° C. for 10 hours was calcined in an electric furnace at 500° C. for 10 hours. The resulting solid i.e., substantially pure titanium oxide was pulverized in a mortar to form a catalyst having a particle diameter of 8 to 16 mesh.

The catalyst (150 ml) was packed into a quartz reaction tube (25 mm in diameter and 500 mm in length), and while passing carbon dioxide gas through the tube at a rate of 500 ml/min., the temperature of the inside of the tube was raised to 450° C. Then, while carbon dioxide gas as a diluent was caused to pass at the same rate, a reaction solution comprising phthalic anhydride and benzene in a mole ratio of 1:25 was gasified and fed over the catalyst at a gas space velocity of 900 $hr^{-1}$ (calculated for NTP). The gas generated as a result of the reaction was cooled and trapped by a condenser, and analyzed by gas chromatography.

The conversion of phthalic anhydride used was found to be 84%, and the selectivity for anthraquinone was 78% and the selectivity for benzophenone was 5%, both based on the phthalic anhydride reacted.

EXAMPLES 2 to 6

The procedure of Example 1 was repeated except that the mole ratio of benzene to phthalic anhydride, the rate of feeding of the starting gas, the type and amount of an inert gas as a diluent, and the reaction temperature were changed as shown in Table 1. the results are also shown in Table 1.

TABLE 1

| Example | Reaction materials Mole ratio of benzene to phthalic anhydride | Amount of feeding (SV, $hr^{-1}$) | Diluent Type | Amount (ml/min.) | Reaction temperature (°C.) | Conversion of phthalic anhydride (%) | Selectivity for anthraquinone (%) |
|---|---|---|---|---|---|---|---|
| 2 | 25 | 900 | $CO_2$ | 500 | 520 | 95 | 84 |
| 3 | 25 | 900 | $N_2$ | 400 | 450 | 82 | 52 |
| 4 | 10 | 850 | $CO_2$ | 400 | 500 | 94 | 79 |
| 5 | 6 | 870 | $CO_2$ | 400 | 490 | 90 | 73 |
| 6 | 6 | 1500 | $CO_2$ | 700 | 550 | 91 | 81 |

EXAMPLE 7

Aqueous ammonia was gradually added dropwise to an aqueous solution of tin chloride (special reagent grade). The resulting precipitate was dried at 130° C. for 6 hours, and calcined in an electric furnace at 450° C. for 10 hours. The resulting solid was pulverized and sieved to form a tin oxide catalyst having a particle diameter of 8 to 16 mesh.

The catalyst was packed into the same type of reaction tube as used in Example 1, and at a reaction temperature of 500° C., phthalic anhydride and benzene were reacted in a carbon dioxide gas carrier. The mole ratio of phthalic anhydride to benzene was adjusted to 1:30, and the gas space velocity calculated for NTP, as a measure of the amount of the starting feed, was adjusted to 750 $hr^{-1}$.

The reaction product trapped was analyzed, and it was found that the conversion of phthalic anhydride was 95%, the selectivity for anthraquinone was 76%, and the selectivity for benzophenone was 8%.

EXAMPLES 8 to 13

A metal hydroxide gel obtained by adding ammonia to each of various mineral acid metal salts or sulfuric acid was added to the dried titanium oxide prepared in Example 1, and the mixture was kneaded by a mixing and grinding machine, dried at 150° c. for 24 hours, and then molded into tablets (4.8 mm$\phi$ × 5 mm) by means of a tableting machine.

The tablets were calcined at 650° C. for 12 hours, and the strengths of the resulting catalyst tablets were measured. A stainless steel (SUS 304) reaction tube (27 mm in diameter and 700 mm in length) was charged with 150 ml of the catalyst tablets, and phthalic anhydride and benzene were reacted under the same conditions as in Example 1. The results are shown in Table 2.

TABLE 2

| Example | Additive (A) Type | Amount (A/Ti atomic ratio) | Tablet strength (side crush, Kg) | Conversion of phthalic anhydride (%) | Selectivity for anthraquinone (%) |
|---|---|---|---|---|---|
| 8 | Mo | 2/100 | 7.3 | 97 | 69 |
| 9 | W | 1.5/100 | 8.6 | 94 | 59 |
| 10 | Ca | 2/100 | 13.5 | 65 | 84 |
| 11 | Mg | 4/100 | 5.1 | 57 | 89 |
| 12 | K | 1.0/100 | 7.4 | 68 | 87 |
| 13 | $SO_4^{--}$ | 5/100 | 4.8 | 95 | 72 |

What we claim is:

1. In a process for producing anthraquinone by reacting phthalic anhydride with benzene, the improvement which comprises contacting a starting gas containing phthalic anhydride and benzene with a catalyst consisting essentially of titanium oxide obtained by washing meta-titanic acid with water and then drying and calcining, or of tin oxide.

2. In a process for producing anthraquinone from phthalic anhydride and benzene, the improvement which comprises contacting a gas containing phthalic anhydride and benzene with a catalyst consisting essentially of titanium oxide or tin oxide.

3. In a process for producing anthraquinone from phthalic anhydride and benzene, the improvement which comprises contacting a gas containing phthalic anhydride and benzene with a catalyst consisting essentially of tin oxide.

4. In a process for producing anthraquinone from phthalic anhydride and benzene, the improvement which comprises contacting a gas containing phthalic anhydride and benzene with a catalyst consisting essentially of (a) titanium oxide or tin oxide and (b) at least one metallic oxide selected from the group consisting of molybdenum oxide, tungsten oxide, calcium oxide, magnesium oxide and potassium oxide.

5. In a process for producing anthraquinone from phthalic anhydride and benzene, the improvement which comprises contacting a gas containing phthalic anhydride and benzene with a catalyst consisting essentially of (a) titanium oxide or tin oxide, (b) at least one metallic oxide selected from the group consisting of molybdenum oxide, tungsten oxide, calcium oxide, magnesium oxide and potassium oxide, and (c) the sulfate group.

6. The process of claim 4 wherein said catalyst consists of a catalytic amount of titanium oxide and at least one of said metallic oxides.

7. The process of claim 4 wherein said catalyst consists of tin oxide and at least one of said metallic oxides.

8. The process of claim 6 wherein the atomic ratio of the metal of said metallic oxide to titanium in said titanium oxide is from 1.0/100 to 4/100.

9. In a process for producing anthraquinone from phthalic anhydride and benzene, the improvement which comprises contacting a gas containing phthalic anhydride and benzene with a catalyst consisting of (a) titanium oxide and (b) at least one metallic oxide selected from the group consisting of molybdenum oxide, tungsten oxide, calcium oxide, magnesium oxide and potassium oxide.

10. The process of claim 3 wherein carbon dioxide is used as a diluent for the reaction.

11. The process of claim 3 wherein said starting gas contains phthalic anhydride and benzene in a mole ratio of from 1:3 to 1:30.

12. The process of claim 3 wherein the reaction is carried out at a temperature of 300° to 600° C.

13. The process of claim 3 wherein said starting gas is fed into the reaction mixture at a space velocity of 500 to 1000 hr$^{-1}$.

* * * * *